US 6,692,471 B2

(12) United States Patent
Boudreaux (10) Patent No.: US 6,692,471 B2
(45) Date of Patent: Feb. 17, 2004

(54) METHOD AND APPARATUS FOR SAFETY CATHETER INSERTION DEVICE

(75) Inventor: Chad P. Boudreaux, Cincinnati, OH (US)

(73) Assignee: Medex, Inc., Carlsbad, CA (US)

( * ) Notice: Subject to any disclaimer, the term of this patent is extended or adjusted under 35 U.S.C. 154(b) by 102 days.

(21) Appl. No.: 09/788,073

(22) Filed: Feb. 16, 2001

(65) Prior Publication Data

US 2002/0115964 A1 Aug. 22, 2002

(51) Int. Cl.[7] .............................................. A61M 5/32
(52) U.S. Cl. ................................... 604/198; 604/164.08
(58) Field of Search ............................ 604/272, 273, 604/274, 264, 158, 161, 162, 164.01, 164.06, 164.08, 164.11, 167.01, 167.03, 168, 110, 198

(56) References Cited

U.S. PATENT DOCUMENTS

| 3,352,306 A | | 11/1967 | Hirsch | |
|---|---|---|---|---|
| 4,610,671 A | | 9/1986 | Luther | |
| 4,627,838 A | * | 12/1986 | Cross et al. | 604/105 |
| 5,085,648 A | * | 2/1992 | Purdy et al. | 604/198 |
| 5,419,766 A | | 5/1995 | Chang et al. | |
| 5,573,510 A | | 11/1996 | Isaacson | |
| 5,601,536 A | | 2/1997 | Crawford et al. | |
| 5,683,365 A | * | 11/1997 | Brown et al. | 604/110 |
| 5,830,190 A | * | 11/1998 | Howell | 604/168.01 |
| 5,906,594 A | * | 5/1999 | Scarfone et al. | 604/165.01 |
| 5,957,892 A | | 9/1999 | Thorne | |
| 6,012,213 A | * | 1/2000 | Chang et al. | 29/447 |
| 6,050,976 A | | 4/2000 | Thorne et al. | |

FOREIGN PATENT DOCUMENTS

EP  0 645 159 A1  3/1995

* cited by examiner

Primary Examiner—Edward K. Look
Assistant Examiner—John K Fristoe, Jr.
(74) Attorney, Agent, or Firm—Wood, Herron & Evans, LLP (57) ABSTRACT

Apparatuses and methods for safely inserting of a catheter into a patient and the use of a solid needle. An exemplary apparatus of the present invention includes a needle shaft, which is coupled to a solid needle tip. The needle shaft includes a first end, a second end, and a first dimension. The solid needle tip includes a sharp end and a blunt end, a groove, and a second dimension. The second dimension is greater than the first dimension such that a juncture, which is a step up from the first end, is formed when the needle shaft is coupled to the solid needle tip. The groove runs axially along a surface of said solid needle tip and extends from said sharp end to said blunt end. A catheter is disposed about the needle shaft and the solid needle tip with the solid needle tip protruding from an edge of the catheter. A connector is used to couple the catheter to a safety container, which is partially disposed within a body. The safety container is designed to trap the solid needle tip therein after the solid needle tip retracts into the safety container.

40 Claims, 8 Drawing Sheets

METHOD AND APPARATUS FOR SAFETY CATHETER INSERTION DEVICE

BACKGROUND OF THE INVENTION

The present invention relates to catheter insertion devices.

Catheters are primarily used to administer fluids, such as medicine, directly into a patient's vascular system. A catheter is typically inserted into a patient's vein using a catheter insertion device that includes a sharp tip needle. Generally, the needle is disposed inside the interior hollow portion of the catheter with its sharp tip slightly protruding beyond the edge of the catheter. The catheter equipped with the needle is connected to a needle hub. The needle is then used to facilitate the insertion of the catheter into a patient and is removed when catheter insertion is successfully achieved.

One problem is that immediately after the withdrawal of the needle from the patient's vein, the clinician performing the catheter insertion for the patient is exposed to the needle tip. Such exposure to the needle tip creates a danger of an accidental needle stick leaving the clinician or others vulnerable to the transmission of dangerous blood-borne pathogens such AIDS and hepatitis.

Several safety catheter insertion devices have been developed.

One example relates to a device equipped with a protection mechanism in which several rigid segments are serially connected to each other by a plurality of hinges. These segments are disposed about the insertion needle. These segments are folded upon each other during the needle insertion and are extended to completely cover the needle once the insertion is completed. (See U.S. Pat. Nos. 5,957,892 and 6,050,976).

Another example relates to a device using a retraction mechanism utilizing power or energy to retract the needle into a housing compartment. (See U.S. Pat. No. 6,050,976). Yet, another example relates to a device with an automatic retraction mechanism through the use of a spring mechanism to enable needle retraction. (See U.S. Pat. No. 5,573,510).

All of these methods relate to implementing a device to retract the needle into a concealed area. These methods require complex assembly of multiple parts and a complicated retracting mechanism, which in turn may make the safety insertion device much more expensive and complicated to use as compared to a conventional insertion device without those safety features. Another problem associated with these safety insertion devices is that the needle may escape from the device thus defeating the safety purpose.

Moreover, conventional needles that are used with safety catheter insertion devices such as those described above are hollow. Hollow needles may break easily thus, exposing the clinician or the patient to more risks of contamination or of injury.

SUMMARY OF THE INVENTION

The present invention provides apparatuses and methods for safely inserting of a catheter into a patient. The present invention further provides apparatuses and methods for safely inserting of a catheter into a patient with the use of a solid needle.

In one exemplary embodiment, an apparatus of the present invention includes a hollow needle shaft which is coupled to a hollow needle tip. The hollow needle shaft includes a first end, a second end, and a first dimension. The hollow needle tip includes a sharp end, a blunt end, and a second dimension. The second dimension is greater than the first dimension such that a juncture, which is a step up from the first end, is formed when the hollow needle shaft couples to the hollow needle tip. A catheter is disposed about the hollow needle shaft and the hollow needle tip with the hollow needle tip protruding from an edge of the catheter. A connector is used to couple the catheter to a safety container, which is partially disposed within a body. The safety container is designed to trap the hollow needle tip therein after the hollow needle tip retracts into the safety container.

In another exemplary embodiment, an apparatus of the present invention includes a needle shaft, which is coupled to a solid needle tip. The needle shaft includes a first end, a second end, and a first dimension. The solid needle tip includes a sharp end, a blunt end, a groove, and a second dimension. The second dimension is greater than the first dimension such that a juncture, which is a step up from the first end, is formed when the needle shaft is coupled to the solid needle tip. The groove runs axially along a surface of said solid needle tip and extends from said sharp end to said blunt end. A catheter is disposed about the needle shaft and the solid needle tip with the solid needle tip protruding from an edge of the catheter. A connector is used to couple the catheter to a safety container, which is partially disposed within a body. The safety container is designed to trap the solid needle tip therein after the solid needle tip retracts into the safety container.

The above features and advantages of the present invention will be apparent from the following detailed description of preferred embodiments. The drawings are not necessarily drawn to scale but the emphasis is being placed upon illustrating the principles of the present invention.

BRIEF DESCRIPTION OF THE DRAWINGS

FIGS. 1A and 1B illustrate exemplary embodiments of a needle assembly according to the present invention.

FIG. 1A-1 illustrates a cross-sectional view of a juncture between a needle tip and a needle shaft of a needle assembly according to one embodiment of the present invention.

FIGS. 2A to 2D illustrate an example of a solid needle assembly according to one embodiment of the invention in four different views. FIG. 2B illustrate a top view; and, FIGS. 2C and 2D illustrate a two-dimensional view and a three-dimensional view of a solid needle tip.

FIG. 4A-1 illustrates a safety container according to one embodiment of the invention with the safety container in an opening position.

FIG. 4A-2 illustrates a safety container according to one embodiment of the invention with the safety container in a closing position.

DETAILED DESCRIPTION OF THE INVENTION

The reference characters refer to the same parts throughout different views of the invention unless indicated otherwise.

Figures 1A, 1A, 1B:
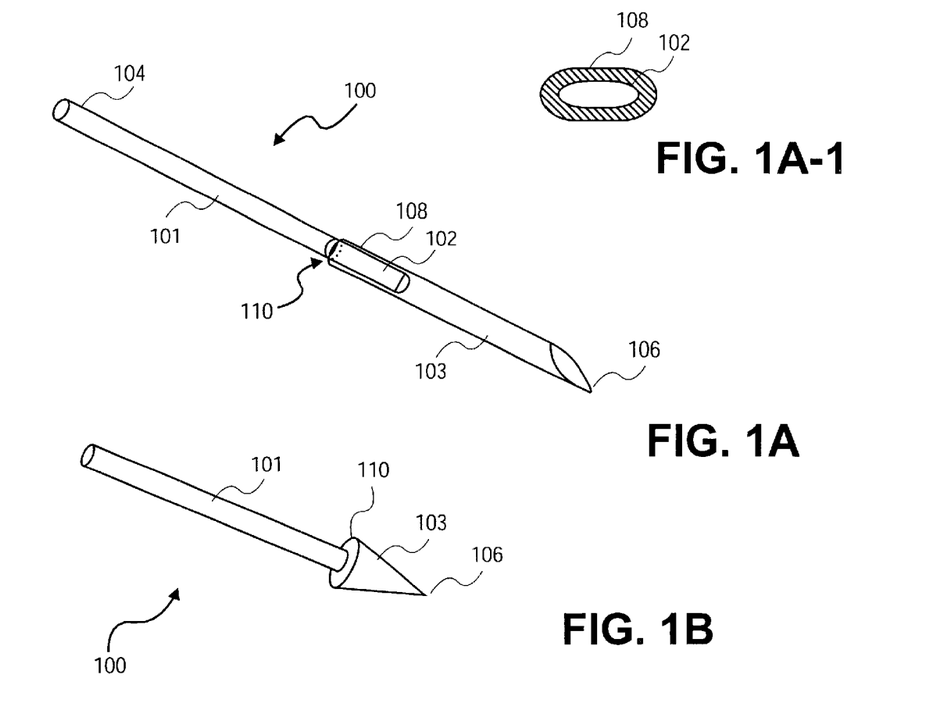

FIG. 1A illustrates, according to one embodiment, components of a safety catheter insertion device 100, which comprises a needle shaft 101 and a hollow needle tip 103. Needle shaft 101 has a first end 102 and a second end 104. Both needle shaft 101 and hollow needle tip 103 may be made out of a metal such as stainless steel. Needle shaft 101 may be hollow or solid.

Hollow needle tip 103 may be an ordinary needle tip typically used by a clinician for inserting a catheter into a patient. Hollow needle tip 103 may be about 0.25 inches long. Hollow needle tip 103 has a sharp end 106 and a blunt end 108. Sharp end 106 may have a bevel shape or a V-point shape. As illustrated in FIG. 1A, blunt end 108 of hollow needle tip 103 may be coupled to first end 102 of needle shaft 101.

One problem observed with a conventional needle tip working in conjunction with a safety container is that the needle tip may accidentally be forced to exit the safety container with enough force applied in pulling on the needle during retraction. When that happens, the safety container will not be able to trap the needle, thus, the risk of injury or contamination still persists. One cause associated with this problem is due to the fact that the needle is smooth and there is not a kink, a lip, or a step up from the shaft of the needle to the tip of the needle to prevent the needle from accidentally exiting the safety container. Therefore, it is desirable that a safety catheter insertion device has a needle designed such a way that the needle is trapped within a safety container without the risk of ever being dislodged from the safety container.

According to one embodiment of this invention, at least the dimension of blunt end 108 of hollow needle tip 103 must be greater than the dimension of first end 102 of needle shaft 101. FIG. 1A-1 illustrates a cross-sectional view of needle assembly 100 in which blunt end 108 of hollow needle tip 103 is larger that first end 102 of needle shaft 101. In such an embodiment, when hollow needle tip 103 is affixed or coupled to needle shaft 101, the juncture that is formed between these two elements is juncture 110. Juncture 110 is essentially a step up 230 between needle shaft 101 and hollow needle tip 103.

The coupling of hollow needle tip 103 and needle shaft 101 may create a catheter insertion device having a needle assembly with the shape of an arrow as illustrated in FIG. 1B. This arrow shape catheter insertion needle also has a step up that is juncture 110 which is located between needle shaft 101 to hollow needle tip 103. The step up may be configured into only one side of needle tip 103. Thus, one side of needle assembly 100 may be smooth while the other side may have the step up juncture 110. This step up feature functions as a stop or a latch that prevents needle assembly 100 from accidentally exiting or slipping off from a safety container, as is described below. The step up will latch itself against an exit opening in the safety container through which, needle assembly 100 may be retracted.

A method such as heat shrink or press fit may be employed to couple hollow needle tip 103 to needle shaft 101. In press fitting, hollow needle tip 103 may simply be pressed onto needle shaft 101. In heat shrinking, hollow needle tip 103 which, is made out of metal, may be heated to cause an expansion in the metal. The expanded hollow needle tip 103 may then be coupled to needle shaft 101, and then be allowed to cool or shrink to create a tight fit between these two elements. Alternatively, needle shaft 101 may be glued to hollow needle tip 103 to create a tight coupling between these two elements.

Figures 1C, 1D:
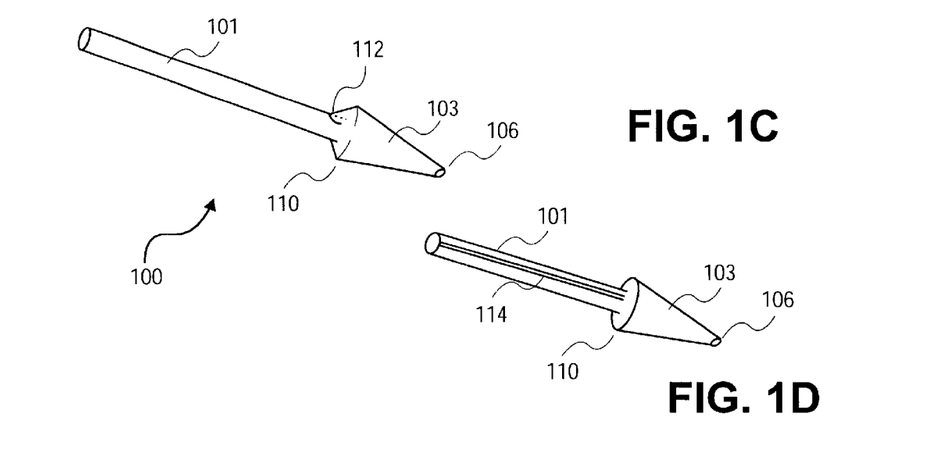
FIGS. 1C and 1D illustrate exemplary embodiments of a needle assembly according to the present invention in which a needle shaft of the needle assembly is a solid needle shaft.

In another example, needle shaft 101 may be solid as opposed to being hollow as discussed above. FIG. 1C illustrates that in the event that needle shaft 101 is solid, needle shaft 101 may have a short slit 112 on a surface of needle shaft 101 and at one end of needle shaft 101, for example, at first end 102. Slit 112 enables fluid or blood to travel from hollow needle tip 103 into a flash chamber (details forthcoming) on the catheter insertion device. Alternatively, needle shaft 101 may be designed with a slit 114 running along the surface of needle shaft 101 as depicted in FIG. 1D. Slit 114 would also enable fluid or blood to travel from the hollow needle tip 103 into a flash chamber (details forthcoming) on the catheter insertion device.

A solid needle shaft may be desirable because it may be sturdier than a hollow needle shaft thus, minimizing risk of breakage or damages due to stress, strain, or bent in needle assembly 100. A solid needle shaft may hence, help to protect a clinician from being exposed to pathogens or subjected to risk of injuries, as well as to prevent damages to the catheter insertion device. Also, when a catheter is transparent, a solid shaft may allow the clinician to see blood flashback sooner.

Figure 2A:
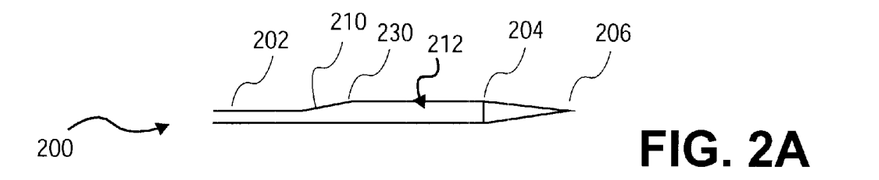
FIG. 2A illustrates a side view.
Figure 2B:
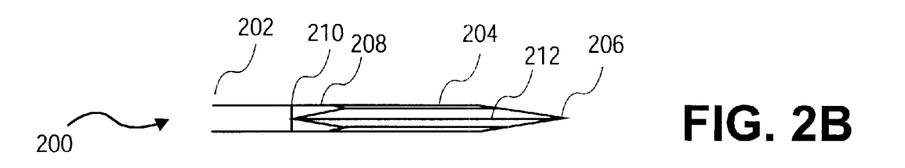
Figure 2C:
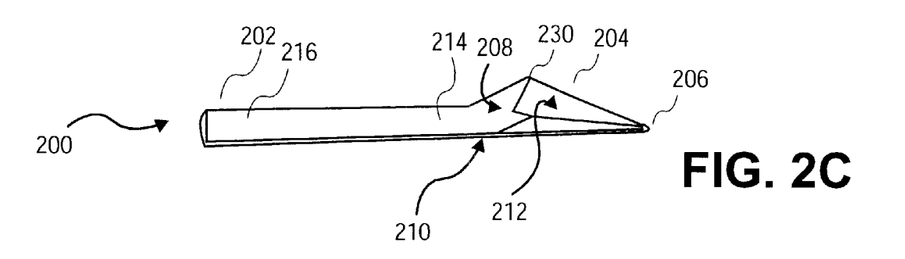
Figure 2D:
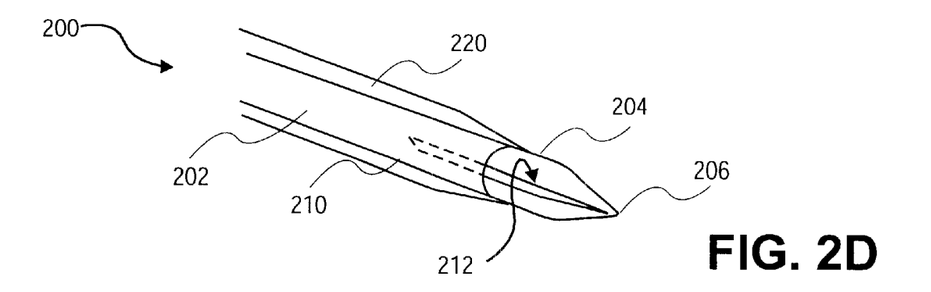

FIGS. 2A to 2D illustrate another embodiment of the present invention. These figures illustrate different views of a needle assembly 200 which may be used for a safety catheter insertion device. Needle assembly 200 comprises a needle shaft 202 and a solid needle tip 204. FIG. 2A shows solid needle tip 204 in a side view; FIG. 2B shows solid needle tip 204 from a top view; and, FIGS. 2C to 2D show solid needle tip 204 in a two-dimensional perspectives and a three-dimensional perspectives. Needle shaft 202 may also be a solid needle shaft having a first end 214 and a second end 216. Both needle shaft 202 and needle tip 204 may be made out of a metal such as stainless steel. As a component of a catheter insertion device, solid needle tip 204 has a sharp end 206 and a blunt end 208. Sharp end 206 may be in the shape of a bevel shape or a V-point tip shape.

FIGS. 2B and 2C illustrate that solid needle tip 204 also has a groove 212. Groove 212 is designed to allow blood or fluid to flow from needle tip 204 into a flash chamber. It is necessary for the clinician inserting the catheter into a patient to see that the needle tip has reached the patient's vein in order to stop advancing the needle tip and begin advancing the catheter into the vein. Thus, it is preferable that blood from the needle tip flow into the flash chamber to indicate to the clinician that the needle tip has reached the patient's vein.

Groove 212 is designed for the purpose of allowing fluid or blood to flow from needle tip 204 down the catheter 220 and into the flash chamber (details forthcoming) of the catheter insertion device. Groove 212 is essentially a "V" shaped notch cut into a surface of needle tip 204 to make a fluid path. Groove 212 thus, would achieve the same purpose that the hollow portion of a hollow needle shaft would provide, i.e., providing a fluid path.

A groove or a slit similar to groove 212 may also be placed on a surface of a needle shaft 202 that is solid. This feature may make the blood flow rate into a catheter and a flash chamber much faster.

As illustrated in FIG. 2C, blunt end 208 of needle tip 204 may be coupled to first end 214 of needle shaft 202. One important feature of this embodiment is that at least the dimension of blunt end 208 of needle tip 204 is greater than the dimension of first end 214. In that event, when needle tip 204 is affixed or coupled to needle shaft 202, the juncture that is formed between these two elements is juncture 210.

Juncture 210 is essentially a step up 230 or a lip between needle shaft 202 and needle tip 204. FIGS. 2C and 2D illustrate that juncture 210 is formed when first end 214 is coupled to blunt end 208. Juncture 210 creates a step up 230 or a lip from needle shaft 202 to needle tip 204 viewing from second end 216 to blunt end 208. In one exemplary embodiment, step up 230 need not be on both side of needle shaft 202. In other words, needle assembly 200 may have a flat bottom surface and the step up 230 is located on the top as shown in FIGS. 2C and 2D. The use of this step up 230 may be designed only for the purpose of preventing needle tip 204 from escaping a safety container. Therefore, having a step up feature on both sides of needle tip 204 may not be necessary.

The coupling of needle tip 204 and needle shaft 202 may create a catheter insertion device having a needle assembly with the shape of a shovel illustrated in FIGS. 2C and 2D. This shovel shape catheter insertion needle has a step up 230 that is juncture 210 which is located between needle shaft 202 to needle tip 204. This step up 230 feature functions as a stop or a latch that prevents needle assembly 200 from accidentally exiting or slipping off from a safety container as explained further below. The step up 230 will latch itself against an exit opening in the safety container through which, needle assembly 200 may be retracted.

Needle tip 204 may be coupled to needle shaft 202 using an ultrasonic welding method well known in the art. Alternatively, needle tip 204 and needle shaft 202 may be formed from one single piece of stainless steel. In such an embodiment, some material is shaved off from one end of this one piece of stainless steel to create needle shaft 202 and some is shaved off from the remaining end to create needle tip 204. For example, as illustrated in FIG. 2C, one end of the piece of stainless steel is shaved off to make the needle shaft portion of needle assembly 200. And, the other end is shaved off to make the needle tip portion of needle assembly 200. Note that needle shaft 202 is much thinner than at least blunt end 208 to create that step up 230 feature discussed above for needle assembly 200. In this embodiment, fluid or blood will flow down from needle tip 204 via groove 212, along needle shaft 202, and into the catheter 220 reaching the flash chamber which is described further below.

Figure 3A:
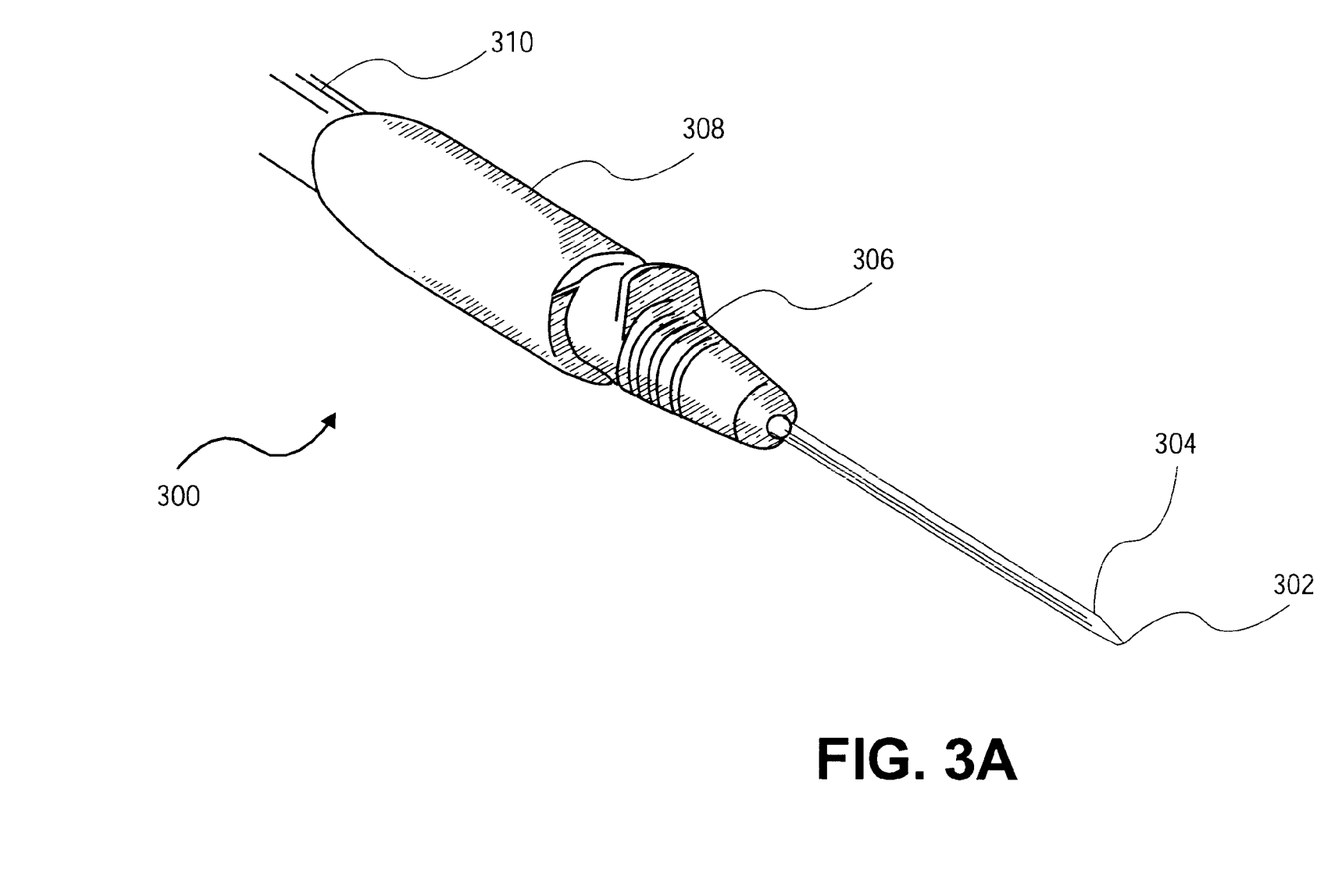
FIG. 3A illustrates an example of a general appearance of a safety catheter assembly according to one embodiment of the invention.

FIG. 3A illustrates an example of a safety catheter assembly 300 according to the present invention. Assembly 300 comprises a body 308, a flash plug 310, a catheter 304, a hub 306 may act as a connector, and a needle assembly having a needle shaft and a needle tip 302 affixed therewith. Assembly 300 further comprises a safety container which is disposed within body 308 and hub 306 (not visually apparent from FIG. 3A, but see below).

Figure 3B:
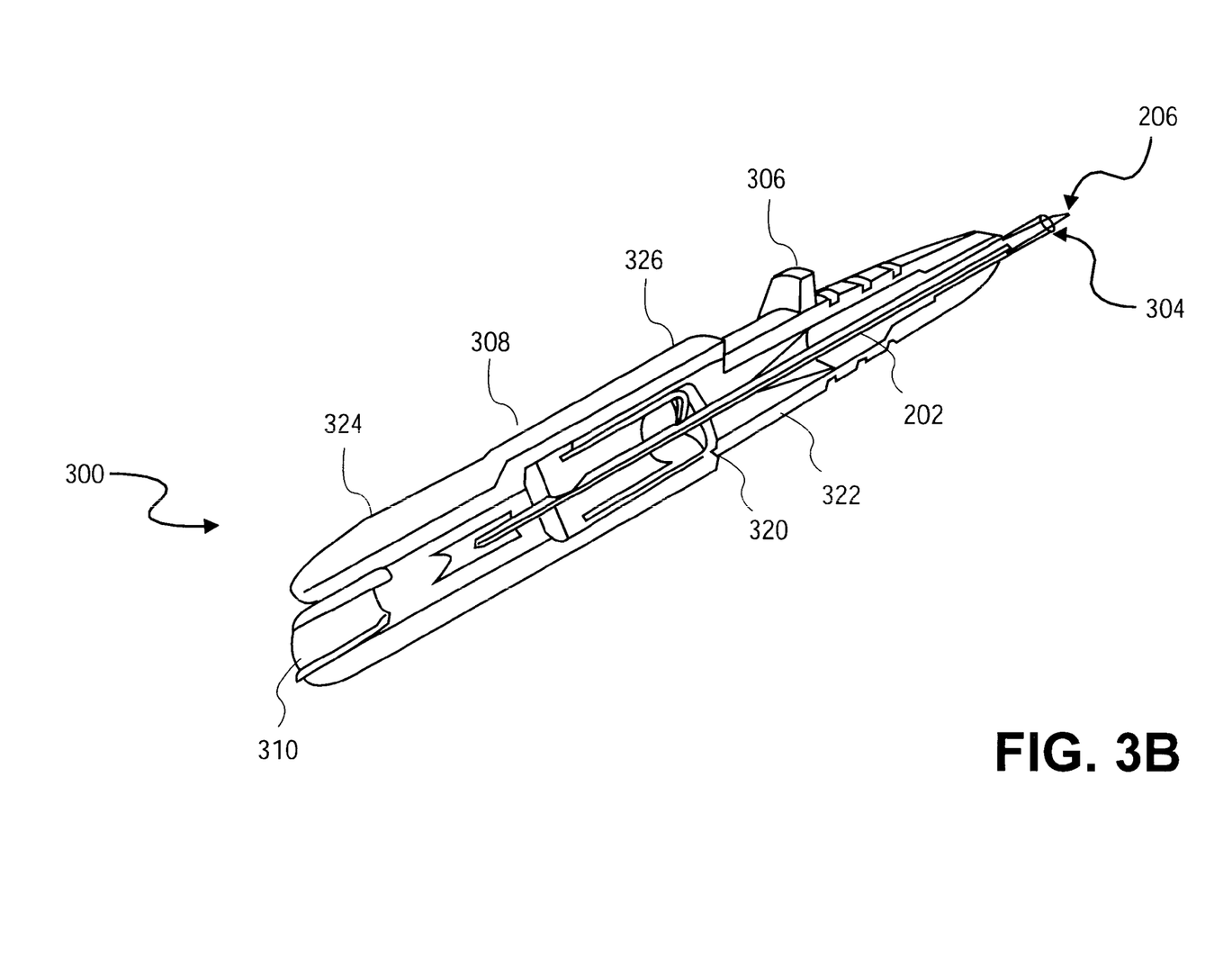
FIG. 3B illustrates a safety catheter assembly according to one embodiment of the invention in a sectional view.
Figure 3C:
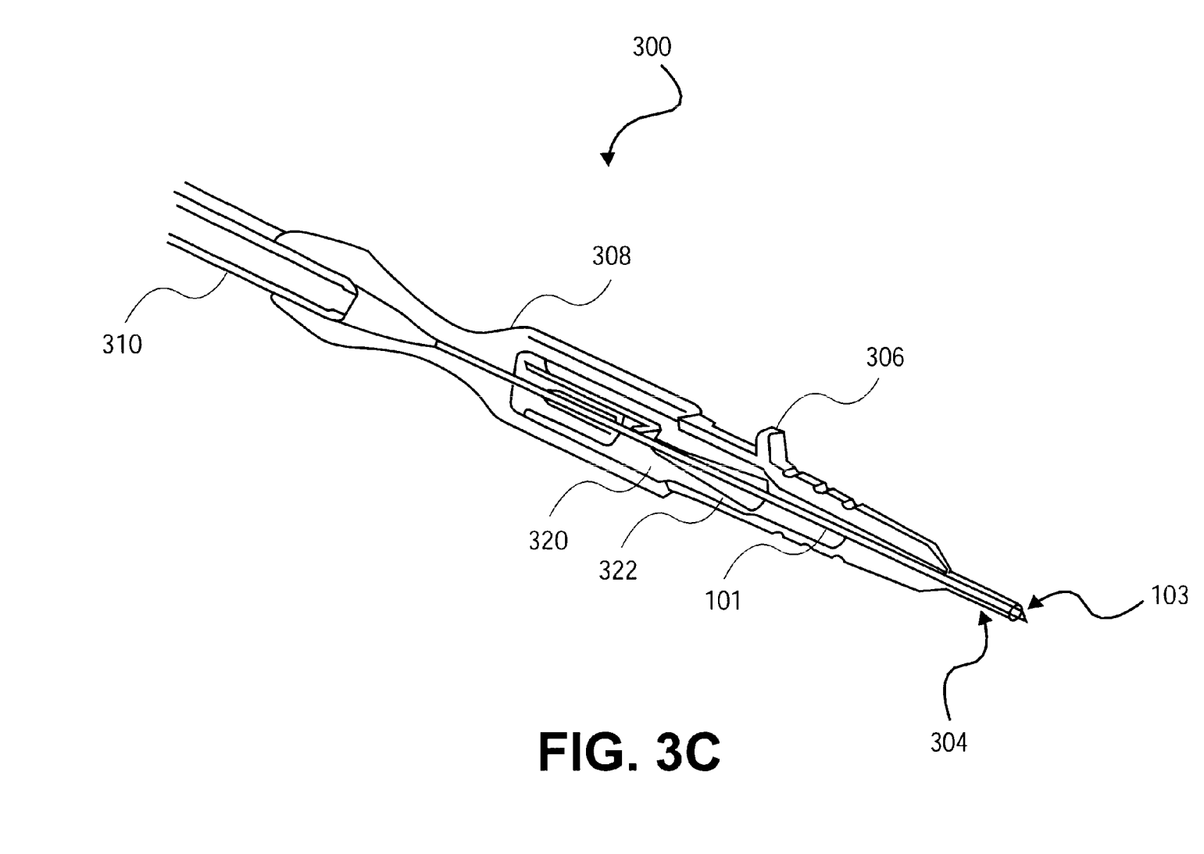
FIG. 3C illustrates a safety catheter assembly according to another embodiment of the invention having an hourglass shape body in a sectional view.

FIGS. 3B to 3C illustrate catheter assembly 300 in more details. Body 308, flash plug 310 and safety container 320 may be made out a plastic material. In a preferred embodiment, flash plug 310 is permeable to air. Catheter 304 is flexible, pliable, and soft, and is made out of a biocompatible material such as a medical grade polyurethane, silastic, silicone rubber or a similar material. And, the needle assembly such as needle assembly 100 or needle assembly 200 may be made out of a metal such as stainless steel (see above).

As illustrated in detain in FIG. 3B, body 308 has a distal end 324 and a proximal end 326. FIG. 3B illustrates a sectional view of a catheter assembly 300. In one example, body 308 is designed so that flash plug 310 may be disposed within distal end 324 of body 308. Body 308 is also designed such that it houses safety container 320, and needle assembly such as needle assembly 100 or needle assembly 200.

Also, as illustrated in FIG. 3B, body 308 is hollow and may have several channels. Safety container 320 may be partially disposed within the hollow portion of body 308 at proximal end 326. The portion of safety container 320 that is not disposed within body 308 may be called a protruding safety container portion 322 or protruding portion 322. Protruding portion 322 couples to hub 306, which in turn couples to catheter 304.

FIGS. 3B to 3C illustrate that a needle assembly may be disposed through catheter 304, through hub 306, through safety container 320 and finally into body 308. A suitable needle assembly may be needle assembly 100 or needle assembly 200 described above. In one example, when needle assembly 200 is used, it would be disposed through catheter 304, hub 306, safety container 320 and finally into body 308. When needle assembly 200 is properly assembled as above, needle tip 204 should extend slightly beyond the edge of catheter 304.

Body 308 is also designed to function as a flash chamber mentioned above. In other words, body 308 is designed to show blood flash back to indicate to the clinician performing the needle tip and the catheter insertion that both units have reached the patient's vein. To function as a flash chamber, body 308 is typically made out of a transparent material in order to indicate blood flash back. Alternatively, body 308 may simple by designed with a small transparent window or a slit along a surface of body 308 to indicate blood flash back.

In an embodiment where hollow needle tip 103 and needle shaft 101 are both hollow, when hollow needle tip 103 has reached a vein, blood will flow up hollow needle tip 103 and needle shaft 101. Blood flash back occurs when the blood spills into body 308. At this point, it is desirable that the clinician knows that hollow needle tip 103 has reached the vein so that the clinician may then stop advancing hollow needle tip 103 and may then begin sliding catheter 304 into the vein.

As mentioned, body 308 may also have channels. In an embodiment where the insertion needle is a solid needle such as needle assembly 200 described above, body 308 nay be designed with two or three channels as shown in FIG. 3B. One channel may be used to only house needle shaft 202. In this embodiment, blood will flow up groove 212. Needle shaft 202 may be a solid needle shaft thus, no blood will travel through. Instead, blood may travel from grove 212 through the other channels in body 308 to indicate blood flash back to the clinician. Alternatively, the channel that houses needle shaft 202 may be large enough so that blood may travel along needle shaft 202 through the same channel.

According to an example of the present invention, flash plug 310 is designed to prevent blood from shooting out of body 308. This is necessary to prevent exposing the clinician to harmful pathogens as well as to minimize contamination. Flash plug 310 is also designed to allow air to flow through to prevent pressure built up in the assembly.

FIG. 3C illustrates that body 308 may have the design of an hourglass shape. This shape may make safety catheter assembly 300 easier to handle and may provide a better grip. The hourglass shaped body 308 may also be more aesthetically pleasing than an ordinary cylindrical shaped body 308.

Catheter 304 may be a typical intravenous catheter to assist in medication injection into a patient. Such a catheter is typically short. In one exemplary embodiment, catheter 304 is disposed about a hollow needle tip 103 such that hollow needle tip 103 extends slightly beyond the edge of the catheter 304 (see FIGS. 3B–3C). Hollow needle tip 103 may be about 0.25 inches long and catheter 304 may preferably be slightly shorter than 0.25 inches. Catheter 304 having hollow needle tip 103 disposed therein is inserted into an ordinary catheter connector such as hub 306.

In both FIGS. 3B and 3C, hub 306 is then coupled to protruding portion 322 thereby affixing needle shaft 101, hollow needle tip 103 and catheter 304 to safety container 320. Safety container 320 is coupled to body 308. Preferably, safety container 320 is designed such that when coupled to body 308, safety container 320 may be detached or slid off from body 308 but not from hub 306. In such a design, safety container is always close to hollow needle tip 103 for the purpose of easily and quickly trapping hollow needle tip 103 after insertion of catheter 304 is achieved.

In another exemplary embodiment, catheter 304 is disposed about needle tip 204 such that needle tip 204 extends slightly beyond the edge of the catheter 304 (see FIGS. 3B–3C). Needle tip 204 may be about 0.25 inches long and catheter 304 may preferably be slightly shorter than 0.25 inches. Catheter 304 having needle tip 204 disposed therein is inserted into an ordinary catheter hub such as hub 306.

In both FIGS. 3B and 3C, hub 306 is then coupled to protruding portion 322 thereby affixing needle shaft 202, needle tip 204 and catheter 304 to safety container 320. Safety container 320 is coupled to body 308. Preferably, safety container 320 is designed such that when coupled to body 308, safety container 320 may be detached or slipped off from body 308 but not from hub 306. In such a design, safety container is always close to needle tip 204 for the purpose of easily and quickly trapping needle tip 204 after insertion of catheter 304 is achieved.

Figure 4A:
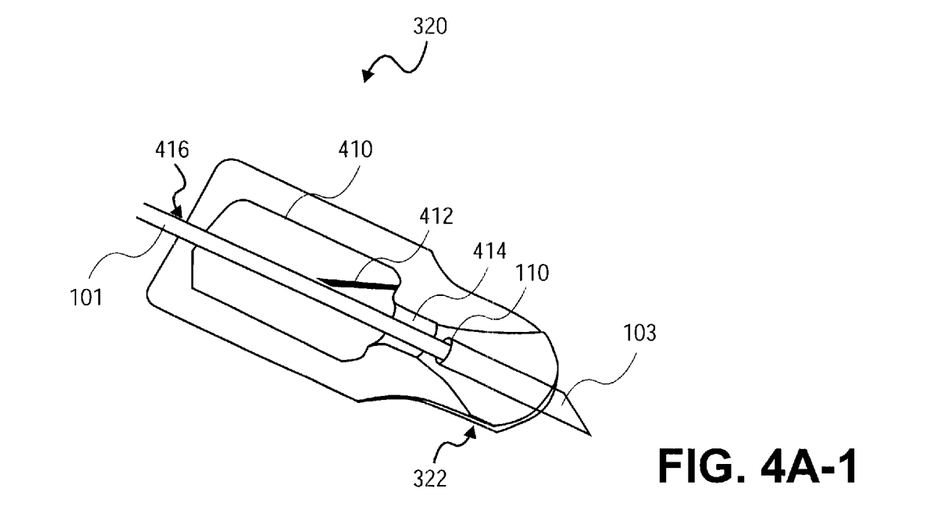
Figure 4A:
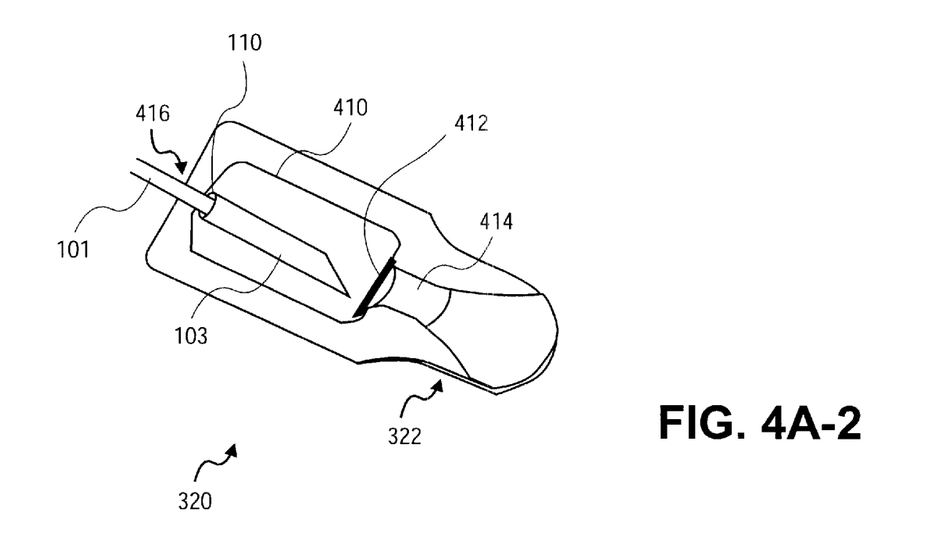

FIGS. 4A-1 and 4A-2 illustrate an example of a safety container 320. In this embodiment, safety container 320 comprises at least one lumen, lumen 410, a gate 412, a front opening 414, and a back opening 416. Lumen 410 may be surrounded by the wall of safety container 320. As described above, safety container 320 is disposed within body 308 leaving a protruding portion 322 (see FIG. 3C). Materials from the wall of safety container 320 may be shaved off to form protruding portion 322. Protruding portion 322 may be shaped like a luer end such that it will be able to fit snuggly into hub 306 (shown in FIGS. 3B and 3C).

FIG. 4A-1 demonstrates that in one example, gate 412 is disposed inside lumen 402 and is swingably affixed to front opening 414. A needle assembly such as needle assembly 100 having needle shaft 101 and hollow needle tip 103 may be disposed through front opening 414, through gate 412, and into safety container 320. When needle assembly 100 is being disposed through safety container 320, needle assembly 100 passes through front opening 414, gate 412, and into lumen 410. As needle assembly 100 is passing through gate 412, it pushes gate 412 away from front opening 414. Safety container 320 is then in the opening position as depicted in FIG. 4A-1.

FIG. 4A-2 then demonstrates safety container 320 in the closing position. After the clinician see the blood flash back through body 308, the clinician will retract needle assembly 100 into safety container 320. As hollow needle tip 103 retracts pass and beyond gate 412 and into lumen 410, gate 412 will swing into a closing position. This feature allows at least the needle tip portion 106 of assembly 100 to be trapped within safety container 320.

FIGS. 4A-1 and 4A-2 illustrate that needle assembly 200 may be used instead of needle assembly 100. Here, FIG. 4A-1 demonstrates that in one example, a needle assembly such as needle assembly 200 having needle shaft 202 and needle tip 204 may be disposed through front opening 414 and into safety container 320. Gate 412 is disposed inside lumen 402 and is swingably affixed to front opening 414. When needle assembly 200 is being disposed through safety container 320, needle assembly 200 passes through front opening 414, gate 412, and into lumen 410. As needle assembly 200 is passing through gate 412, it pushes gate 412 away from front opening 414. Safety container 320 is then in the opening position as depicted in FIG. 4A-1.

FIG. 4A-2 then demonstrates safety container 320 in the closing position. After the clinician sees the blood flash back through body 308, the clinician will retract needle assembly 200 into safety container 320. As needle tip 204 retracts pass and beyond gate 412 and into lumen 410, gate 412 will swing into a closing position. This feature allows at least the needle tip portion 206 of assembly 200 to be trapped within safety container 320.

The swingable gate feature discussed above also allows safety container 320 to stay clean and free of blood residue. When a needle shaft passes through gate 412, blood on the outside of the needle shaft is wiped against gate 412 thus, blood is contained within safety container 320. The clinician thus may handle safety container 320 having a needle tip trapped inside without risk of exposure to harmful pathogens.

One advantage of needle assembly 100 or needle assembly 200 is that there is a step up juncture such as set up 230 from the needle shaft to the needle tip. One main objective for a safety catheter insertion device is to enclose the needle tip after the catheter has been successfully inserted into the patient. The needle tip according to the present invention is designed such that needle can be trapped within the safety container without the risk of being dislodged during retraction.

As illustrated in FIGS. 4A-1 and 4A-2, in one exemplary embodiment, to effectively trap hollow needle tip 103 within lumen 410, back opening 416 of safety container is designed such that only needle shaft 101 may fit through. Since hollow needle tip 103 would have a blunt end's dimension that is larger than that of needle shaft 101, when the needle shaft and the needle tip couple to each other, juncture 110 would have a dimension that is larger than back opening 416. Thus, as needle assembly 100 is being retracted, juncture 110 will not pass through back opening 416. Therefore, hollow needle tip 103 will be safely trapped within safety container 320.

In an example where needle assembly 200 is used, to effectively trap needle tip 204 within lumen 410, back opening 416 of safety container is designed such that only needle shaft 202 may fit through. Since needle tip 204 would have a blunt end's dimension that is larger than that of needle shaft 202, when the needle shaft and the needle tip couple to each other, juncture 210 would have a dimension that is larger than back opening 416. Thus, as needle assembly 200 is being retracted, juncture 210 will not pass through back opening 416. Therefore, needle tip 204 will be safely trapped within safety container 320.

FIGS. 4B to 4E illustrate another example of a safety container 320 in several different sectional views. In this embodiment, safety container 320 comprises a nose 400, a nose cap 430, a clip 406, a front opening 404 and a back opening 408. Nose 400 and nose cap 430 may be made out of a plastic material. Clip 406 may be made out of plastic, mylar, metal, smooth metal, or stainless steel.

In one embodiment, nose 400 further includes a first lumen 402 which is surrounded by wall 403 of nose 400. Nose 400 includes a first luer end 420, which is the part of safety container 320 that couples to a catheter hub. Nose 400 also includes a second luer end 421, which is the part of safety container 320 that is slidably coupled to body 308. Safety container 320 is slidably coupled to body 308 for the purpose that during the insertion of a needle and a catheter into the patient, safety container 320 will stay close to the needle, and that facilitates quick and easy trapping of the needle tip into safety container 320. When the needle tip has to be retracted from the patient, the clinician may pull on a body 308 to retract the needle shaft that is disposed within a safety container 320 which is partially and sidably disposed inside body 308. With little force, body 308 may slide off safety container 320 and the needle shaft may be retracted while the safety container holding the needle tip is still coupled to the hub and the catheter.

Nose cap 430 is disposed within first lumen 402. Nose cap 430 further includes a second lumen 432, which is surrounded by wall 434 of nose cap 430. Clip 406 is disposed within first lumen 402 and is positioned on a surface of the wall 434. One function of nose cap 430 is to hold clip 406 in place inside lumen 402. Nose cap 430 may also function to reduce the size of back opening 408 such that there is only an exit large enough for a needle shaft such as needle shaft 101 of assembly 100 or needle shaft 202 of assembly 200.

Figure 4B:
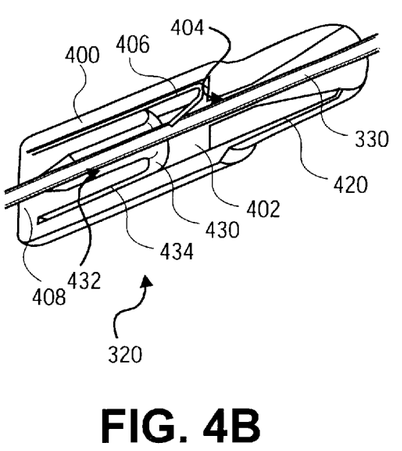
FIGS. 4B to 4E illustrate examples of a safety container according to another embodiment of the invention, all in sectional views.
Figure 4C:
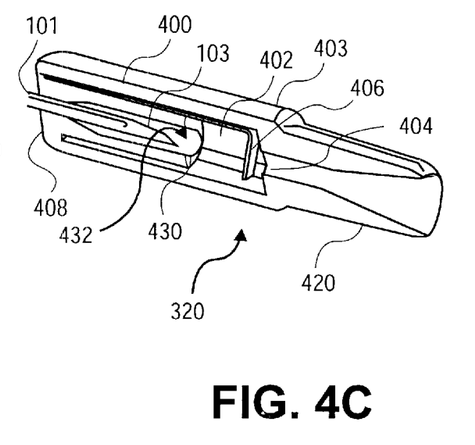
Figure 4D:
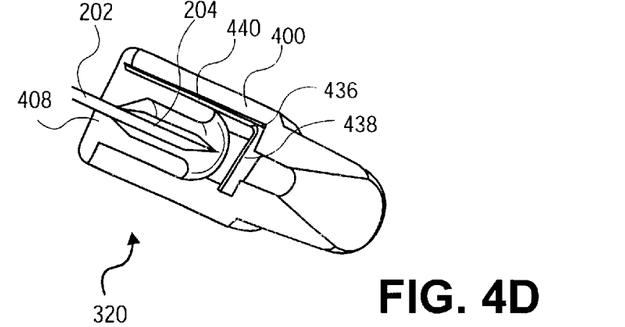
Figure 4E:
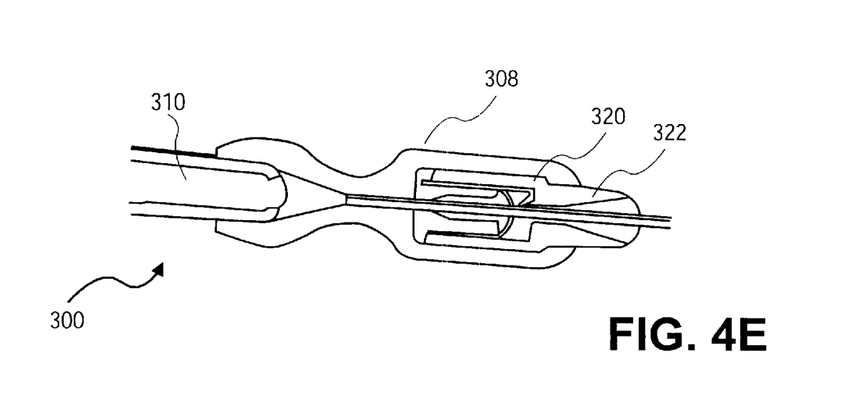
Figures 5A, 5B, 5C, 5D, 5E, 5F, 5G:
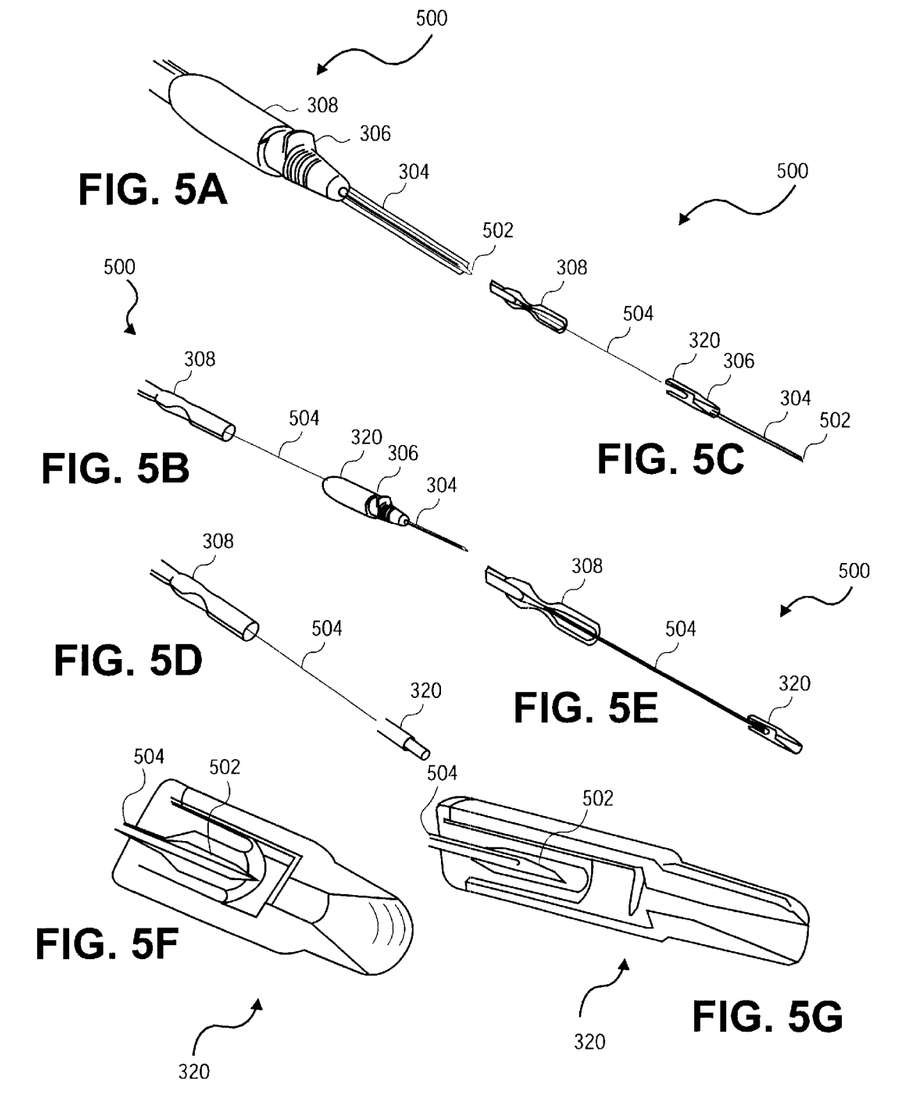
FIGS. 5A–5G illustrate a method to trap a catheter insertion needle tip in a safety container according to one embodiment of the invention in different views.

As illustrated in FIGS. 4B to 4E, clip 436 may be disposed inside lumen 402 and resting against nose cap wall 434. FIG. 4D shows that clip 436 may include a first leg 438 and a second leg 440. Clip 436 may be made out of one single piece of plastic, mylar, or metal, such as stainless steel, that is bent at a knee portion to give first leg 438 and second leg 440. Alternatively, clip 436 may be formed from two pieces of material joined at one point.

In one example, clip 436 may have the shape of an "L" or a "J" depending on whether it is in the opening or closing position. Clip 436 may be designed such that first leg 438 swings backward from its original position, position "L", when a needle assembly is being disposed through front opening 404. For instance, clip 436 bends as a needle assembly is being disposed through. Thus, clip 436 changes from an "L" shape to a "J" shape.

FIG. 4B also depicts that in one example clip 436 is in the opening position as a needle shaft 330 is being inserted through safety container 320. In that event, clip 436 has a "J" shape. FIGS. 4C and 4D then depict clip 436 in the closing position trapping hollow needle tip 103 or needle tip 204 inside safety container 320. Here, clip 436 would have an "L" shape. This feature allows a needle tip, such as hollow needle tip 103 or needle tip 204, to be trapped within safety container 320.

This feature also allows safety container 320 to stay clean and free of blood residue. When a needle shaft such as needle shaft 101 or needle shaft 202 passes through gate 412, residual blood on the outside of the needle shaft is wiped against gate 412 thus, the blood is contained within safety container 320. The clinician thus may handle safety container 320 having the needle tip trapped inside with low risk of exposure to harmful pathogens.

As mentioned, one advantage of needle assembly 100 or needle assembly 200 is that there is a step up 230 from the needle shaft to the needle tip. One main objective for a safety catheter insertion device is to enclose the needle tip after the catheter has been successfully inserted into the patient. A needle tip according to the present invention is designed such that needle can be trapped within the safety container without the risk of being dislodged during retraction.

As illustrated in FIGS. 4B to 4E, in one exemplary embodiment, to effectively trap hollow needle tip 103 or needle tip 204 within first lumen 402, back opening 408 of safety container is designed such that only a needle shaft such as needle shaft 101 or 202 may fit through. In essence, nose cap 430 has an exit that is only large enough for the needle shaft to slide through.

In such an embodiment, a needle tip such as hollow needle tip 103 or needle tip 204 would have a blunt end's dimension that is larger than that of a needle shaft 101 or needle shaft 204. Hence, when the needle shaft and the needle tip are coupled to each other, the juncture formed would have a dimension that is larger than back opening 408. Thus, as the needle assembly is being retracted, hollow needle tip 103 or needle tip 204 will not pass through back opening 408 but will be safely trapped within safety container 320.

Needle assembly 100 (see FIGS. 1A–1D) according to these embodiments may be designed such that if a strong force is applied in pulling or retracting needle shaft 101, hollow needle tip 103 will detach or break off from needle shaft 101. In that way, only needle shaft 101 will exit the safety container 320.

Similarly, needle assembly 200 (see FIGS. 2A–2D), according to these embodiments, may be designed such that if a strong force is applied in pulling or retracting needle shaft 202, needle tip 204 will detach or break off from needle shaft 202. In that way, only needle shaft 202 will exit the safety container 320.

FIGS. 5A–5G illustrate an exemplary method according to the present invention for safely inserting of a catheter into a patient utilizing an insertion device having a needle tip. Safety catheter insertion device 500 may be provided fully assembled according to the embodiments described above. Device 500 may include a body 308, a safety container 320, a hub 306, a catheter 304, a needle tip 502 and a needle shaft 504 (see FIG. 5A). Note that needle tip 502 may be hollow needle tip 103 or needle tip 204 discussed above. And, needle shaft 504 may be needle shaft 101 or needle shaft 202 discussed above.

When needle tip 502 positioned in an interior hollow portion of the catheter 304, its tip may extend slightly beyond the edge of the catheter 304 such that a clinician may insert needle tip 502 and catheter 304 into a patient. Body 308 may act as a handle to assist the clinician in the maneuvering of needle tip 502 and catheter 304 into a vein of the patient.

When needle tip 502 has punctured a vein, blood will shoot out into body 308 which is transparent or which has a window so as to indicate to the clinician that needle tip 502 has reached the patient's vein. At this point, the clinician may manually slide catheter 304 into the vein of the patient by using his or her fingers.

When catheter insertion is accomplished, the clinician depresses down onto hub 306 and catheter 304, and manually withdraws needle tip 502 from the patient by pulling on body 308 which houses needle shaft 504 and retracting needle shaft 504 away from the patient. Needle tip 502 is then retracted into safety container 320 and trapped inside safety container 320. The clinician may continue to pull on body 308 so that needle shaft 504, but, needle tip 502 will not exit safety container 320 because of the of the step up 230 designed into needle tip 502 and needle shaft 504 as discussed above.

The clinician may then remove safety container from hub 306 by pulling on body 308 and needle shaft 504 with enough force. A safety container 320 is detached from hub 306 and catheter 304, catheter 304 and hub 306 would remain with the patient. Needle tip 502 will be safely trapped within safety container 320 (See FIGS. 5D–5G). The clinician may also detach needle shaft 504 from needle tip 502 by applying more force on body 308 and/or needle shaft 504. Alternatively, needle shaft 504 may be physically broken off needle tip 502. Safety container 320 may thus contains only needle tip 502 afterward.

The clinician may then dispose of safety container 320 along with needle tip 502. The clinician may then hook up an I.V. drip to hub 306 to allow fluid or medicine to be injected into the patient through catheter 304.

We claim:

1. An assembly comprising:
   a one-piece needle shaft extending between a first end and a second end, the first end having a first dimension;
   a separate one-piece needle tip having a sharp end and a blunt end, said blunt end having a second dimension that is greater than said first dimension of the needle shaft, the blunt end of the needle tip being attached to the first end of the needle shaft to form a juncture, said juncture being a step up from said needle shaft first end to said needle tip blunt end;
   a catheter disposed about said needle shaft and said needle tip; and
   a connector to couple said catheter to a safety container which is partially disposed within a body, said safety container being designed to trap said needle tip therein after said needle tip retracts into said safety container.

2. An assembly as in claim 1 wherein said safety container further comprising:
   a first lumen;
   a front opening wherethrough said needle shaft and said needle tip being disposed;
   at least a gate disposing within said first lumen and coupling to said front opening, said gate being designed such that when said needle shaft and said needle tip are being disposed through said front opening said gate swings backward away from an original closing position and when at least said needle tip sufficiently retracts into said first lumen said gate returns to said original closing position to trap said needle tip therein; and
   a back opening having an opening dimension that is smaller than said juncture to stop said juncture and said needle tip from exiting said back opening.

3. An assembly as in claim 2 wherein said first lumen is a nose having a luer end to couple to said connector, said nose further comprising a nose cap being disposed therein, said nose cap including a second lumen, and being configured to accept said needle shaft and said needle tip, and to define said back opening in a manner that stops said juncture and said needle tip from exiting said back opening from inside said second lumen.

4. An assembly as in claim 3 wherein said gate is a clip having two legs, one of said two legs being disposed within said first lumen between said nose and said nose cap to secure said clip, the other leg of said two legs disposing about said original closing position.

5. An assembly as in claim 4 wherein said needle shaft is a solid needle shaft having a slit on a surface of said solid needle shaft.

6. An assembly as in claim 5 wherein said body including a distal end, a proximal end wherethrough said safety container being partially disposed, and at least one transparent portion.

7. An assembly as in claim 6 further comprising a plug being disposed within said distal end, said plug being air permeable.

8. An assembly as in claim 7 wherein said body has an hourglass shape design.

9. An assembly as in claim 1, where said needle tip is hollow.

10. An assembly as in claim 1, where said needle shaft is hollow.

11. An assembly comprising:
    a needle shaft having a first end, a second end, and a first dimension;
    a solid needle tip, said solid needle tip having a sharp end and a blunt end, and a groove, said blunt end having a second dimension that is greater than said first dimension to couple to said first end to form a juncture, said juncture being a step up from said first end, and said groove being disposed radially inwardly and running axially along a surface of said solid needle tip and extending from said sharp end to said blunt end;
    a catheter disposed about said needle shaft and said solid needle tip with said solid needle tip protruding from an edge of said catheter; and
    a connector to couple said catheter to a safety container which is partially disposed within a body, said safety container being designed to trap said needle tip therein after said solid needle tip retracts into said safety container.

12. An assembly as in claim 11 wherein said safety container further comprising:
    a first lumen;
    a front opening wherethrough said needle shaft and said solid needle tip being disposed;
    at least a gate disposing within said first lumen and coupling to said front opening, said gate being designed such that when said needle shaft and said solid needle tip are being disposed through said front opening said gate swings backward away from an original closing position and when said solid needle tip sufficiently retracts into said first lumen said gate returns to said original closing position to trap said solid needle tip therein; and
    a back opening having an opening dimension being smaller than said juncture to stop said juncture and said solid needle tip from exiting said back opening.

13. An assembly as in claim 12 wherein said first lumen is a nose having a luer end to couple to said connector, said nose further comprising a nose cap being disposed therein, said nose cap including a second lumen and being configured to accept said needle shaft and said solid needle tip, and to define said back opening in a manner that stops said juncture and said needle tip from exiting said back opening from inside said second lumen.

14. As assembly as in claim 13 wherein said gate is a clip having two legs, one of said two legs being disposed within said first lumen between said nose and said nose cap to secure said clip, the other leg of said two legs disposing about said original closing position.

15. As assembly as in claim 14 wherein said needle shaft is a solid needle shaft having a slit on a surface of said solid needle shaft.

16. An assembly as in claim 15 wherein said body including a distal end, a proximal end wherethrough said safety container being partially disposed, and at least one transparent portion.

17. As assembly as in claim 16 further comprising a plug being disposed within said distal end, said plug being air permeable.

18. An assembly as in claim 17 wherein said body has an hourglass shape design.

19. A method comprising:
coupling a one-piece needle shaft to a separate one-piece needle tip, said needle shaft extending between a first end and a second end, the first end having a first dimension, said needle tip having a sharp end, a blunt end, and a second dimension that is greater than said first dimension of the needle shaft such that said coupling forms a juncture that is a step up from said needle shaft first end to said needle tip blunt end;
disposing a catheter about said needle shaft and said needle tip; and
connecting said catheter to a safety container which is partially disposed within a body using a connector, said safety container being designed to trap said needle tip therein after said needle tip retracts into said safety container.

20. A method as in claim 19 further comprises:
designing said safety conatiner to include a first lumen; a front opening wherethrough said needle shaft and said needle tip being disposed; an gate disposing therein and coupling to said front opening, said gate being designed such that when said needle shaft and said needle tip are being retracted pass said front opening said gate swings backward away from an original closing position and when at least said needle tip sufficiently retracts into said first lumen said gate returns to said original closing position to trap said needle tip therein; and a back opening having an opening dimension that is smaller than said juncture to stop said juncture and said hollow needle tip from exiting said back opening.

21. A method as in claim 20 where in said designing said safety container further comprising:
designing said first lumen to be a nose having a luer end to couple to said connector; and
disposing a nose cap within said nose, said nose cap including a second lumen and being configured to accept said needle shaft and said needle tip, and to define said back opening in a manner that stops said juncture and said needle tip from exiting said back opeining from inside said second lumen.

22. A method as in claim 21 further comprising:
configuring said gate to be a clip having two legs, one of said two legs being disposed within said first lumen between said nose and said nose cap to secure said clip and the other leg of said two legs disposing about said original closing position.

23. A method as in claim 22 further comprising:
configuring said needle shaft to be a solid needle shaft having a slit on a surface of said solid needle shaft.

24. A method as in claim 23 further comprising:
configuring said body to include a distal end, a proximal end wherethrough said safety container being partially disposed, and at least one transparent portion.

25. A method as in claim 24 further comprising:
disposing a plug within said distal end, said plug being air permeable.

26. A method as in claim 25 further comprising:
designing said body to have an hourglass shape design.

27. A method as in claim 26 further comprising:
inserting a needle tip into a surface to create an entrance;
advancing a catheter into said entrance;
retracting said needle tip from said entrance once said catheter is inserted into said entrance by pulling a needle shaft in a direction away from said entrance;
retracting said needle shaft and said needle tip through a front opening and into a safety container such that a juncture and said needle tip being trapped inside said safety container by a closed gate; and
removing said safety container from a connector.

28. A method of safely inserting a catheter assembly as in claim 27 wherein said needle tip is solid.

29. A method as in claim 19, wherein said needle tip is hollow.

30. A method as in claim 19, wherein said needle tip is solid.

31. A method as in claim 19, wherein the needle shaft is hollow.

32. A method comprising:
coupling a needle shaft to a solid needle tip, said needle shaft having a first end, a second end, and a first dimension, said solid needle tip having a sharp end, a blunt end, a groove, and a second dimension that is greater than said first dimension such that said coupling forms a juncture that is a step up from said first end, said groove being disposed radially inwardly and running axially along a surface of said solid needle tip and extending from said sharp end to said blunt end;
disposing a catheter about said needle shaft and said solid needle tip with said solid needle tip protruding from an edge of said catheter; and
connecting said catheter to a safety container which is partially disposed within a body using a connector, said safety container being designed to trap said solid needle tip therein after said needle tip retracts into said safety container.

33. A method as in claim 32 where in said coupling of said catheter to said safety container further comprising:
designing said safety conatiner to include a first lumen; a front opening wherethrough said needle shaft and said solid needle tip being disposed; a gate disposing therein and coupling to said front opening, said gate being designed such that when said needle shaft and said solid needle tip are being retracted pass said front opening said gate swings backward away from an original closing position and when at least said solid needle tip sufficiently retracts into said first lumen said gate returns to said original closing position to trap said solid needle tip therein; and a back opening having an opening dimension that is smaller than said juncture to stop said juncture and said solid needle tip from exiting said back opening.

34. A method as in claim 33 where in said designing said safety container further comprising:
designing said first lumen to be a nose having a luer end to couple to said connector; and
disposing a nose cap within said nose, said nose cap including a second lumen and being configured to accept said needle shaft and said solid needle tip, and to define said back opening in a manner that stops said juncture and said solid needle tip from exiting said back opening from inside said second lumen.

35. A method as in claim 34 further comprising:

configuring said gate to be is a clip having two legs, one of said two legs being disposed within said first lumen between said nose and said nose cap to secure said clip and the other leg of said two legs disposing about said original closing position.

36. A method as in claim 35 further comprising:

configuring said needle shaft to be a solid needle shaft having a slit on a surface of said solid needle shaft.

37. A method as in claim 36 further comprising:

configuring said body to include a distal end, a proximal end wherethrough said safety container being partially disposed, and at least one transparent portion.

38. A method as in claim 37 further comprising:

disposing a plug within said distal end, said plug being air permeable.

39. A method as in claim 38 further comprising:

designing said body to have an hourglass shape design.

40. A method as in claim 39 further comprising:

inserting said solid needle tip into a surface to create an entrance;

advancing said catheter into said entrance;

retracting said solid needle tip from said entrance once said catheter is inserted into said entrance by pulling said needle shaft in the direction away from said entrance;

retracting said needle shaft and said solid needle tip through said front opening and into said safety container such that said juncture and said solid needle tip being trapped inside said safety container; and removing said safety container from said connector.

* * * * *

UNITED STATES PATENT AND TRADEMARK OFFICE
CERTIFICATE OF CORRECTION

PATENT NO.    : 6,692,471 B2
DATED         : February 17, 2004
INVENTOR(S)   : Chad P. Boudreaux It is certified that error appears in the above-identified patent and that said Letters Patent is hereby corrected as shown below:

Column 1,
Line 24, "such AIDS and hepatitis." should read -- such as AIDS and hepatitis. --
Line 53, "Hollow needles may break easily thus, exposing" should read -- Hollow needles may break easily, thus exposing --

Column 3,
Line 36, "has a needle designed such a way" should read -- has a needle designed in such a way --
Line 45, "tip 103 is larger than first end 102" should read -- tip 103 is larger than first end 102 --
Line 65, "safety container through which, needle assembly 100" should read -- safety container through which needle assembly 100 --

Column 4,
Line 3, "hollow needle tip 103 which, is made out of metal," should read -- hollow needle tip 103, which is made out of metal, --
Line 24, "hollow needle shaft thus, minimizing risk of" should read -- hollow need shaft, thus minimizing risk of --
Line 26, "A solid needle shaft may hence, help to protect" should read -- A solid needle shaft may hence help to protect --
Line 40, "in a two-dimensional perspectives and a three-dimensional perspectives." should read -- in a two-dimensional perspective and a three-dimensional perspective. --
Line 63, "Groove 212 thus, would achieve" should read -- Groove 212 thus would achieve --

Column 5,
Line 16, "on both side of needle shaft 202." should read -- on both sides of needle shaft 202. --
Line 35, "safety container through which, needle assembly" should read -- safety container through which needle assembly --
Line 63, "may be made out a plastic material" should read -- may be made out of a plastic material --

Column 6,
Line 4, "As illustrated in detain in FIG. 3B," should read -- As illustrated in detail in FIG. 3B, --
Line 36, "body 308 may simple by designed" should read -- body 308 may simply be designed --
Line 54, "solid needle shaft thus, no blood will" should read -- solid needle shaft, thus no blood will --

UNITED STATES PATENT AND TRADEMARK OFFICE
CERTIFICATE OF CORRECTION

PATENT NO. : 6,692,471 B2
DATED : February 17, 2004
INVENTOR(S) : Chad P. Boudreaux It is certified that error appears in the above-identified patent and that said Letters Patent is hereby corrected as shown below:

Column 8,
Line 2, needle tip 103 retracts pass and beyond" should read -- needle tip 103 retracts past and beyond --
Line 22, "tip 204 retracts pass and beyond" should read -- tip 204 retracts past and beyond --
Line 30, "wiped against gate 412 thus, blood is" should read -- wiped against gate 412, thus blood is --
Line 37, "juncture such as set up 230 from" should read -- juncture such as step up 230 from --

Column 9,
Line 64, "against gate 412 thus, the blood is" should read -- against gate 412, thus the blood is --

Column 10,
Line 50, "When needle tip 502 positioned" should read -- When needle tip 502 is positioned --

Column 11,
Lines 3-4, "so that needle shaft 504, but, needle tip 502 will not exit safety container 320 because of the of the step up 230" should read -- so that needle shaft 504, but not needle tip 502, will exit safety container 320 because of the step up 230 --
Line 10, "hub 306 and catheter 304, catheter 304 and hub 306" should read -- hub 306 and catheter 304; catheter 304 and hub 306 --
Line 17, "Safety container 320 may thus contains only" should read -- Safety container 320 may thus contain only --
Line 22, "We claim:" should read -- I claim: --

Column 12,
Line 65, "As assembly as in" should read -- An assembly as in --

Column 13,
Line 3, "As assembly as in" should read -- An assembly as in --
Line 10, "As assembly as in" should read -- An assembly as in --
Line 34, "disposed; an gate disposing" should read -- disposed a gate disposing --
Line 36, "being retracted pass said front" should read -- being retracted past said front --
Line 44, "claim 20 where in said designing" should read -- claim 20 wherein said designing --
Line 54, "opeining from inside" should read -- opening from inside --

UNITED STATES PATENT AND TRADEMARK OFFICE
CERTIFICATE OF CORRECTION

PATENT NO.     : 6,692,471 B2
DATED          : February 17, 2004
INVENTOR(S)    : Chad P. Boudreaux It is certified that error appears in the above-identified patent and that said Letters Patent is hereby corrected as shown below:

<u>Column 14,</u>
Line 45, "where in said coupling" should read -- wherein said coupling --
Line 47, "safety container to include" should read -- safety container to include --
Line 52, "being retracted pass said front" should read -- being retracted past said front --
Line 61, "where in said designing" should read -- wherein said designing --

<u>Column 15,</u>
Line 5, "said gate to be is a clip having" should read -- said gate to be a clip having --

Signed and Sealed this

Twenty-second Day of June, 2004

JON W. DUDAS
*Acting Director of the United States Patent and Trademark Office*